United States Patent [19]
Barriere et al.

[11] Patent Number: 5,994,299
[45] Date of Patent: *Nov. 30, 1999

[54] CYCLOSPORIN COMPOUNDS, THEIR PREPARATION AND THE PHARMACEUTICAL COMPOSITIONS WHICH CONTAIN THEM

[75] Inventors: Jean-Claude Barriere, Bures sur Yvette; Georges Bashiardes, Thiais; Jean-Christophe Carry, Meudon; Michel Evers, La Queue En Brie; Bruno Filoche, Creteil; Serge Mignani, Chatenay-Malabry, all of France

[73] Assignee: Rhone-Poulenc Rorer, S.A., Antony Cedex, France

[*] Notice: This patent is subject to a terminal disclaimer.

[21] Appl. No.: 08/997,612

[22] Filed: Dec. 23, 1997

[30] Foreign Application Priority Data

Dec. 24, 1996 [FR] France .................................. 96 15955

[51] Int. Cl.⁶ .............................. A61K 37/02; C07K 5/12
[52] U.S. Cl. ................................. 514/11; 514/9; 530/317
[58] Field of Search ................................. 530/317; 514/9, 514/11

[56] References Cited

U.S. PATENT DOCUMENTS

| | | | |
|---|---|---|---|
| 4,703,033 | 10/1987 | Seebach ..................................... | 514/11 |
| 4,771,122 | 9/1988 | Seebach .................................. | 530/317 |
| 4,814,323 | 3/1989 | Andrieu et al. ........................... | 514/11 |

FOREIGN PATENT DOCUMENTS

| | | |
|---|---|---|
| A 0484281 | 5/1992 | European Pat. Off. .. |
| A-0484281 | 5/1992 | European Pat. Off. .. |
| 95111162.4 | 7/1995 | European Pat. Off. .. |
| WO 97/04005 | 2/1997 | WIPO . |

OTHER PUBLICATIONS

Billich et al, J. of Virology, Apr. 1995, pp. 2451–2461.
Billich et al., "Mode of Action of SDZ NIM 811, a Non-immunosuppressive Cyclosporin A Anaolog with Activity Against Human Immunodeficiency Virus (HIV) Type 1: Interference with HIV Protein Cyclophilin A Interactions," J. of Virology, 69(4):2451–2461, (1995).
Papageorgiou et al., "Anti HIV–1 Activity of a Hydrophilic Cyclosporin Derivative With Improved Binding Affinity to Cyclophilin A," Bioorganic & Medicinal Chemistry Letters, 6(1):23–26 (1996).
Mikol et al., "The Role of Water Molecules in the Structure–Based Design of (5–Hydroxynorvaline)–2–cyclosporin: Synthesis, Biological Activity, and Crystallographic Analysis With Cyclophilin A," J. Med. Chem., 38(17):3361–3367 (1995).

Primary Examiner—Cecilia J. Tsang
Attorney, Agent, or Firm—Finnegan, Henderson, Farabow, Garrett & Dunner, L.L.P.

[57] ABSTRACT

Cyclosporin compounds of formula (I):

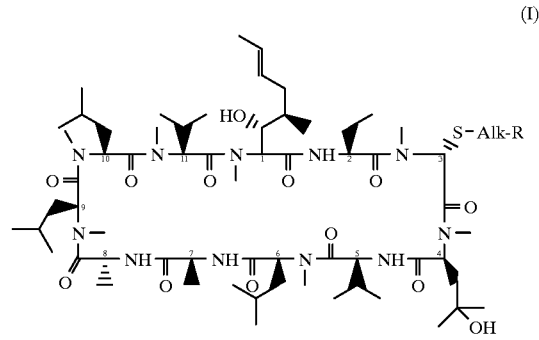

wherein Alk and R are as defined herein, or a pharmaceutically acceptable salt thereof, which derivatives are useful in the treatment and/or prophylaxis of retrovirus infections.

22 Claims, No Drawings

CYCLOSPORIN COMPOUNDS, THEIR PREPARATION AND THE PHARMACEUTICAL COMPOSITIONS WHICH CONTAIN THEM

The technology involved in this application is related to that disclosed in the following co-pending U.S. applications, filed on even date herewith:

(1) Title: Cyclosporin Compound, Its Preparation and the Pharmaceutical Compositions Which Contain It Inventors: Jean-Claude Barriere, Georges Bashiardes, Jean-Christophe Carry, Michel Evers, Bruno Filoche, and Serge Mignani U.S. patent application Ser. No. 08/997,613, filed Dec. 23, 1997

Attorney Docket No.: 03805.0419

(2) Title: Cyclosporin Compounds, Their Preparation and the Pharmaceutical Compositions Which Contain Them Inventors: Jean-Claude Barriere, Georges Bashiardes, Jean-Christophe Carry, Michel Evers, Bruno Filoche, U.S. patent application Ser. No. 08/996,699, filed Dec. 23, 1997. Jean-Pierre Leconte, and Serge Mignani Attorney Docket No.: 03806.0421

The specifications of these related applications are hereby specifically incorporated by reference.

The present invention relates to novel cyclosporin compounds of general formula (I):

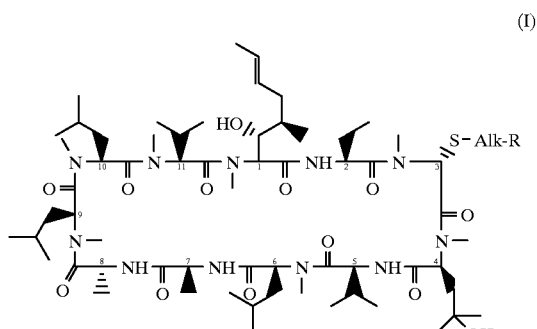

(I)

to their salts, to their preparation and to the pharmaceutical compositions which contain them.

The inventive compounds are useful in the treatment and/or prophylaxis of retrovirus infections, and more particularly of AIDS (acquired immunodeficiency syndrome) and of associated syndromes [ARC (AIDS related complex)]. The inventive compounds exhibit the advantage of being very weakly immunosuppressing.

Cyclosporin derivatives modified at the 3-position have been previously described as immunosuppressants, in European Patent EP 194,972.

Variously modified cyclosporin derivatives, in particular the [4'-hydroxy-MeLeu]$^4$-cyclosporin derivative, have been described previously in European Patent EP 484,281 and in Eur. J. Immunol., 17, 1359 (1987). These derivatives are useful in the treatment of AIDS and are not immunosuppressing.

A description has been given, in Bioorganic and Medicinal Chemistry Letters, 6(1), 23–26 (1996), of the cyclosporin derivative of formula:

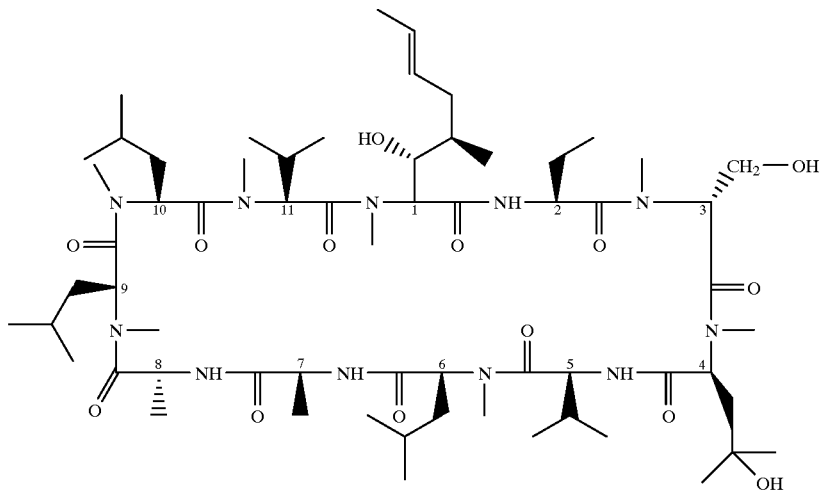

which possesses an anti-HIV-1 activity.

It has now been found that the cyclosporin derivatives of general formula (I), in which:

Alk represents an alkylene radical containing 2 to 6 straight- or branched-chain carbon atoms or a cycloalkylene radical containing 3 to 6 carbon atoms, and R represents either a hydroxyl, carboxyl or alkyloxycarbonyl radical, or an —NR$_1$R$_2$ radical in which R$_1$ and R$_2$, which are identical or different, represent hydrogen atoms or alkyl, alkenyl (2 to 4C), cycloalkyl (3 to 6C) or optionally substituted (by a halogen atom, alkyloxy, alkyloxycarbonyl, amino, alkylamino or dialkylamino) phenyl radical, or represent a benzyl or heterocyclyl radical, wherein the heterocyclyl radical is saturated or unsaturated and contains 5 or 6 ring members and 1 to 3 heteroatoms, preferably chosen from nitrogen, oxygen and sulphur, or in which R$_1$ and R$_2$ form, with the nitrogen atom to which they are attached, a saturated or unsaturated heterocycle containing 4 to 6 ring members, which heterocycle can contain another heteroatom chosen from nitrogen, oxygen and sulphur, optionally substituted by an alkyl, phenyl or benzyl radical, in which R and Alk are defined as above, the functional groups of which that are capable of interfering with the reaction have, if appropriate, been protected beforehand, with an activated form of a [4'-hydroxy-MeLeu]⁴-cyclosporin compound of formula (II):

(II)

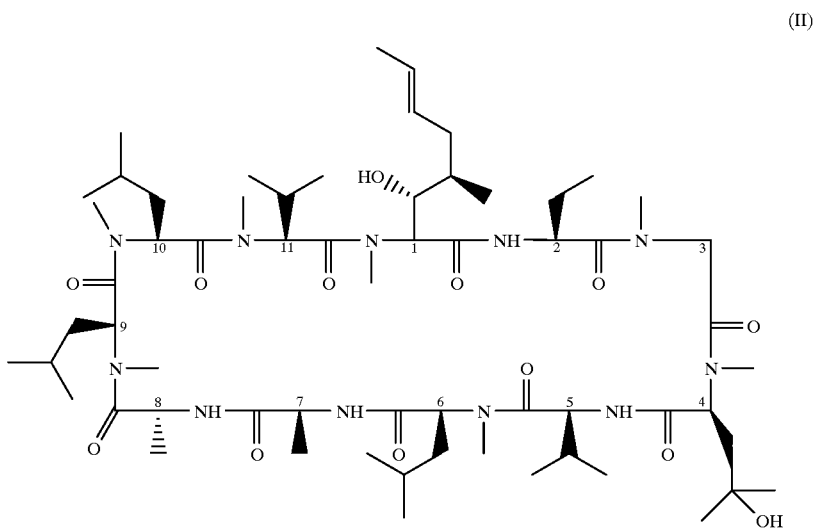

or a radical of general formula (I'):

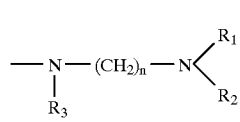

(I')

in which $R_1$ and $R_2$ are defined as above, $R_3$ represents a hydrogen atom or an alkyl radical, and n is an integer from 2 to 4;

wherein the alkyl portions or radicals defined above are straight or branched and contain 1 to 4 carbon atoms;

and their pharmaceutically acceptable salts, when they exist, are particularly advantageous due to their powerful activity and their very weak immunosuppressing nature.

In the formula (I), when $R_1$ and/or $R_2$ represent a heterocyclyl radical, such radical can advantageously be chosen from pyridyl, tetrahydropyridyl, piperidyl, imidazolyl, oxazolyl and thiazolyl.

When $R_1$ and $R_2$ form a heterocyclyl with the nitrogen atom to which they are attached, by way of example, the heterocyclyl radical can be chosen from azetidinyl, piperidyl, piperazinyl, N-methylpiperazinyl, N-phenylpiperazinyl, N-benzylpiperazinyl, pyridyl, imidazolyl, morpholino, thiomorpholino, tetrahydropyridyl, methyltetrahydropyridyl, for example 4-methyltetrahydropyridyl, and phenyltetrahydropyridyl, for example 4-phenyltetrahydropyridyl.

According to the present invention, the products of general formula (I) can be obtained by reaction of a disulphide of general formula (III):

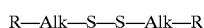   (III)

and then, if appropriate, the protective radical(s) is (are) removed.

The activated form of the cyclosporin of formula (II) is understood to mean a form activated on the sarcosine at the 3-position. This activated form is preferably prepared in situ. Activation is generally carried out under an inert atmosphere, by treatment with an organometallic derivative, in particular a lithium derivative, such as n-butyllithium, lithium diisopropylamide or a mixture, for example. It is also possible to prepare the activated form of the cyclosporin of general formula (II) in liquid ammonia in the presence of an alkali metal amide, for example, sodium or lithium, at a temperature ranging from −32 to −38° C. in an ether, in particular tetrahydrofuran, t-butyl ethyl ether or a mixture.

The addition of the disulphide of general formula (III) is advantageously carried out in an organic solvent, such as a hydrocarbon, for example, hexane, or an ether, for example, diethyl ether, tetrahydrofuran or t-butyl methyl ether, at a temperature ranging from −78 to 0° C. It is sometimes preferable to carry out the operation under nitrogen.

When the substituents of the R radical can interfere with the reaction, it is preferable to protect them beforehand with compatible radicals which can be put in place and removed without affecting the remainder of the molecule. Moreover, the hydroxyl radicals present on the cyclosporin can optionally be protected by any group which does not interfere with the reaction. By way of example, the protective groups can be chosen from the radicals described by T. W. Greene, Protective Groups in Organic Synthesis, J. Wiley-lnterscience Publication (1991), or by McOmie, Protective Groups in Organic Chemistry, Plenum Press (1973).

The [4'-hydroxy-MeLeu]⁴-cyclosporin derivative of formula (II) can be prepared as described in European Patent Application EP 484,281, the disclosure of which is incorporated herein by reference.

In the case where R is a hydroxyl radical, it is also possible to reverse the 2 reaction steps, the derivative modified on the sarcosine at the 3-position being prepared and then hydroxylation being carried out. Hydroxylation is carried out as mentioned above for the preparation of the compound of formula (II).

The disulphide of general formula (III) can be prepared according to or by analogy with the methods described in the examples below.

The novel cyclosporin compounds of formula (I) can be purified, if appropriate, by physical methods, such as crystallization or chromatography.

The cyclosporin compounds according to the invention in which R is carboxyl can be converted into metal salts or into addition salts with a nitrogenous base according to methods known per se. These salts can be obtained by the action of a metal base, for example, an alkali metal or alkaline-earth metal, of ammonia or of an amine on a product according to the invention, in an appropriate solvent, such as water or an alcohol. The resulting salt precipitates after optional concentration of the solution and is separated by filtration.

Mention may be made, as examples of pharmaceutically acceptable salts, of the salts with alkali metals, e.g., sodium, potassium or lithium, or with alkaline-earth metals, e.g., magnesium or calcium, the ammonium salt or the salts of nitrogenous bases, e.g., ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine.

The cyclosporin compounds according to the invention in which R is $NR_1R_2$ can be converted into addition salts with acids by known methods. It is understood that these salts also come within the scope of the present invention.

Mention may be made, as examples of addition salts with pharmaceutically acceptable acids, of the salts formed with inorganic acids, e.g., hydrochlorides, hydrobromides, sulphates, nitrates or phosphates, or with organic acids, e.g., succinates, fumarates, tartrates, acetates, propionates, maleates, citrates, methanesulphonates, ethanesulphonates, p-toluenesulfonates, isethionates or embonates, or with substitution derivatives of these compounds.

The novel cyclosporin compounds according to the present invention are particularly useful in the prophylaxis and treatment of retrovirus diseases and more particularly of AIDS and of associated syndromes. Prophylaxis is understood to mean in particular the treatment of subjects who have been exposed to HIV viruses, in particular asymptomatic seropositives who present the risk of developing the disease in the months or years to come after the primary infection.

The products according to the invention display an anti-retrovirus activity at concentrations devoid of any cytotoxic or cytostatic effect.

The activity of the products of formula (I) has been demonstrated in the techniques described by Pauwells et al., J. Virol. Meth., 20, 309 (1988) and by O. Schwatz et al., AIDS Research and Human Retroviruses, 4(6) 441–48 (1988) and cited by J. F. Mayaux et al., Proc. Nat. Acad. Sci. USA, 91, 3564–68 (1994), the disclosure of each of which is incorporated herein by reference. In these techniques, the products according to the present invention have proved to be active at concentrations of 10 to 350 nM ($IC_{50}$).

The products of formula (I) in which:

Alk represents an alkylene radical containing 2 to 6 straight- or branched-chain carbon atoms, and R represents either a hydroxyl radical, or an $—NR_1R_2$ radical in which $R_1$ and $R_2$, which are identical or different, represent a hydrogen atom or an alkyl, alkenyl (2 to 4 C) or optionally substituted (by a halogen atom, alkyloxy, alkyloxycarbonyl, amino, alkylamino or dialkylamino) phenyl radical, or represent a benzyl radical, or in which $R_1$ and $R_2$ form, with the nitrogen atom to which they are attached, a saturated or unsaturated heterocycle containing 4 to 6 ring members, which heterocycle can contain another heteroatom chosen from nitrogen, oxygen and sulphur, optionally substituted by an alkyl radical, the alkyl portions or radicals defined above being straight or branched and containing 1 to 4 carbon atoms; and their pharmaceutically acceptable salts, when they exist, are particularly preferred.

More preferred are the cyclosporin compounds of formula (I) in which:

Alk represents an alkylene radical containing 2 to 5 straight- or branched-chain carbon atoms, and R represents either a hydroxyl radical, or an $—NR_1R_2$ radical in which $R_1$ and $R_2$, which are identical or different, represent a hydrogen atom or an alkyl, allyl, phenyl or benzyl radical, or in which $R_1$ and $R_2$ form, with the nitrogen atom to which they are attached, a heterocycle chosen from azetidinyl, piperidyl, piperazinyl, N-methylpiperazinyl, N-phenylpiperazinyl, N-benzyl-piperazinyl, morpholino, tetrahydropyridyl, methyltetrahydropyridyl and phenyltetrahydropyridyl, the alkyl portions or radicals defined above being straight or branched and containing 1 to 4 carbon atoms, and their pharmaceutically acceptable salts, when they exist.

Among these more preferred compounds, particularly preferred compounds are the cyclosporin derivatives listed below:

[(R)-2-(N,N-dimethylamino)ethylthio-Sar]$^3$-[4'-hydroxy-MeLeu]$^4$-cyclosporin A;

[(R)-2-(1-piperidyl)ethylthio-Sar]$^3$-[4'-hydroxy-MeLeu]$^4$-cyclosporin A;

[(R)-2-(N-methyl-N-t-butylamino)ethylthio-Sar]3-[4,-hydroxy-MeLeu]4cyclosporin A;

[(R)-2-(hydroxy)ethylthio-Sar]$^3$-[4'-hydroxy-MeLeu]$^4$-cyclosporin A; and

[(R)-2-(N,N-diethylamino)ethylthio-Sar]$^3$-[4'-hydroxy-MeLeu]$^4$-cyclosporin A; and their pharmaceutically acceptable salts.

The following examples, given without implied limitation, illustrate the present invention.

EXAMPLE 1

[(R)-2-(N,N-Dimethylamino)ethylthio-Sar]$^3$-[4'-hydroxy-MeLeu]$^4$-cyclosporin A was prepared according to the following method:

15.4 cm$^3$ of a 1.6M solution of n-butyllithium in hexane were added over 10 minutes to a solution, cooled to a temperature in the region of −10° C. and under nitrogen, of 3.5 cm$^3$ of diisopropylamine (distilled beforehand over calcium hydride) in 45 cm$^3$ of tetrahydrofuran (distilled beforehand over sodium), the temperature being maintained at 0° C. The mixture was stirred at 0° C. for 20 minutes and was then cooled to a temperature in the region of −78° C. The solution thus obtained was transferred, under nitrogen, via a transfer tube, onto a solution of 2 g of [4'-hydroxy-MeLeu]$^4$-cyclosporin A in 40 cm$^3$ of tetrahydrofuran cooled beforehand to a temperature in the region of −76° C., the temperature being maintained at approximately −70° C. The resulting mixture was stirred at −75° C. for 5 minutes and then 7.2 cm$^3$ of a 1.6M solution of n-butyllithium in hexane were added over 10 minutes. Stirring was maintained for 10 minutes and then 6.85 g of commercially available di(2-N,N-dimethylaminoethyl) disulphide were added over 10 minutes, the temperature being maintained at approximately −75° C. The mixture was stirred at a temperature in the region of −78° C. for 30 minutes and then at 0° C. for 18 hours. 40 cm$^3$ of distilled water, to which 36% aqueous hydrochloric acid had been added, were poured onto the reaction mixture, maintained at 0° C., in order to obtain a pH in the region of 7. The mixture was separated by settling and the aqueous phase was washed with 30 cm$^3$ of diethyl ether. The organic extracts were combined, washed with 30 cm$^3$ of a saturated sodium chloride solution, dried over sodium sulphate, filtered and concentrated under reduced pressure (2.7 kPa) at a temperature in the region of 40° C. The yellow oil obtained was taken up in 40 cm$^3$ of toluene and 300 cm$^3$ of distilled water to which 36% hydrochloric acid had been added in order to obtain a pH in the region of 2. The phases were separated by settling. The aqueous phase was washed again with 40 cm$^3$ of toluene and the toluene phases were combined. The latter were washed with 50 cm$^3$ of distilled water acidified to a pH in the region of 2. The aqueous phases were combined, 50 cm$^3$ of toluene were added and then neutralization was carried out with an aqueous sodium bicarbonate solution. The organic phase was separated by settling and the aqueous phase was washed twice with 30 cm$^3$ of toluene. The organic phases were combined, dried over sodium sulphate, filtered and concentrated under reduced pressure (2.7 kPa) at a temperature in the region of 40° C. to give a solid which was purified by flash chromatography on a silica column (0.04–0.063 mm) (eluent: dichloromethane/methanol 98/2 by volume and then dichloromethane/methanol 95/5), 10-cm$^3$ fractions were collected. The fractions containing the expected product were combined and concentrated under reduced pressure (2.7 kPa) at a temperature in the region of 40° C. to give a solid which is triturated in 3 cm$^3$ of pentane. After filtration, 74 mg of [(R)-2-(N,N-dimethylamino)-ethylthio-Sar]$^3$-[4'-hydroxy-MeLeu]$^4$-cyclosporin A were obtained in the form of a white solid that melted at approximately 140° C.

$^1$H N.M.R. spectrum (400 MHz, CDCl$_3$, δ in ppm): 1.23 (d, J=7 Hz, 3H, 8β CH$_3$), 1.33 (d, J=7.5 Hz, 3H, 7δ CH$_3$), 1.60 (d, J=5 Hz, 3H, CH$_3$ at 1γ), 1.68 and 2.36 (2 dd, J=15 and 6.5 Hz, each 1 H, 4β CH$_2$), 2.23 (broad s, 6H, N(CH$_3$)$_2$ of the 2-dimethylaminoethylthio at 3α), 2.40 (mt, 1H, 5β CH), from 2.48 to 2.86 (mt, 4H, SCH$_2$CH$_2$N of the 2-dimethylaminoethylthio at 3α), 2.68, 3.09, 3.16, 3.22, 3.42 and 3.47 (6 s, respectively 6H, 3H, 3H, 3H, 3H and 3H, 7 NCH$_3$), 3.63 (d, J=6 Hz, 1H, OH at 1β CH), 3.72 (mt, 1H, 1β CH), 4.52 (mt, 1H, 7α CH), 4.61 (t, J=9 Hz, 1H, 5α CH), 4.81 (mt, 1H, 8α CH), 4.95 (dd, J=9 and 6 Hz, 1H, α CH of a leucine), from 5.00 to 5.10 (mt, 2H, 2α CH and α CH of a leucine), 5.10 (d, J=11 Hz, 1H, 11α CH), from 5.20 to 5.35 (mt, 2H, CH═CH), 5.40 (t, J=6.5 Hz, 1 H, 4α CH), 5.47 (d, J=6 Hz, 1H, 1α CH), 5.68 (dd, J=10.5 and 4 Hz, 1H, α CH of a leucine), 5.96 (s, 1H, CH at 3α), 7.12 (d, J=8Hz, 1H, CONH at 8), 7.46 (d, J=9 Hz, 1H, CONH at 5), 7.60 (d, J=7.5 Hz, 1H, CONH at 7), 7.92 (d, J=9.5 Hz, 1H, CONH at 2).

[4'-Hydroxy-MeLeu]$^4$-cyclosporin A was prepared as described in European Patent Application EP 484,281, the disclosure of which is incorporated herein by reference.

EXAMPLE 2

[(R)-2-(1-Piperidyl)ethylthio-Sar]$^3$-[4'-hydroxy-MeLeu]$^4$-cyclosporin A was prepared according to the following method:

100 mg of sodium metal and then 100 mg of ferric nitrate were added to 100 cm$^3$ of ammonia maintained at a temperature in the region of −33° C. As soon as the blue coloration of the mixture had disappeared, 1.45 g of sodium metal were added over 20 minutes. The mixture was stirred at −33° C. for 1 hour, a solution of 5 g of [4'-hydroxy-MeLeu]$^4$-cyclosporin A in 75 cm$^3$ of tetrahydrofuran was added dropwise over approximately 15 minutes and then a solution of 5.92 g of di[2-(1-piperidyl)ethyl] disulphide in 25 cm$^3$ of dioxane was added over 10 minutes. The reaction mixture was stirred at a temperature in the region of −33° C. for 90 minutes and then 5 g of solid ammonium chloride were added portionwise. The ammonia was allowed to evaporate with stirring, the temperature of the mixture changed from −33 to 25° C. over 2 hours. The mixture was filtered and the filtrate was concentrated under reduced pressure (2.7 kPa) at a temperature in the region of 35° C. The residual yellow oil (12.3 g) was triturated with 50 cm$^3$ of pentane. The solid which had formed was filtered off. The solid was triturated with a mixture of 50 cm$^3$ of pentane and 50 cm$^3$ of hexane. The solid was filtered off and then again triturated with 25 cm$^3$ of heptane. The solid was dissolved in 250 cm$^3$ of t-butyl methyl ether and the solution was filtered. The filtrate was concentrated under reduced pressure (2.7 kPa) at a temperature in the region of 40° C. and resulted in 5.52 g of a pale-yellow foam. The solid was purified by chromatography on a column of neutral alumina (eluent: ethyl acetate/cyclohexane 4/1 by volume), 10-cm$^3$ fractions were collected. The fractions containing the expected product were concentrated under reduced pressure (2.7 kPa) at a temperature in the region of 40° C. The solid obtained (1.86 g) was stirred for 1 hour with 25 cm$^3$ of acetone and then filtered off and dried under reduced pressure (5 kPa) at a temperature in the region of 35° C. 1.72 g of [(R)-2-(1-piperidyl)ethyl-thio-Sar]$^3$-[4'-hydroxy-MeLeu]$^4$-cyclosporin were thus obtained in the form of a yellow solid that melted at a temperature in the region of 143° C.

$^1$H N.M.R. spectrum (400 MHz, CDCl$_3$, δ in ppm): 1.35 (d, J=7.5 Hz, 3H, 7β CH$_3$), 1.62 (d, J=5 Hz, 3H, 7η CH$_3$), 1.71 (dd, J=15 and 6.5 Hz,1 H corresponding to 1H of the 4β CH$_2$), from 2.20 to 3.10 (mt, the 8H corresponding to the SCH$_2$CH$_2$N and to the 2 NCH$_2$ of the piperidine), 2.70, 3.12, 3.22, 3.25, 3.45 and 3.50 (6 s, respectively 6H, 3H, 3H, 3H, 3H and 3H, the 7 NCH$_3$), 3.66 (d, J=6 Hz, 1H, OH at 1β), 3.73 (mt, 1H, 1β CH), 4.54 (mt, 1H, 7α CH), 4.62 (broad t, J=9 Hz, 1H, 5α CH), 4.83 (mt, 1H, 8α CH), 4.97 (dd, J=8 and 6 Hz, 1H, α CH of a leucine), from 5.00 to 5.10 (mt, 2H, α CH of a leucine and 2α CH), 5.13 (d, J=11 Hz, 1H, 1α CH), from 5.25 to 5.40 (mt, 2H, CH═CH), 5.42 (t, J=6.5 Hz, 1H, 4α CH), 5.50 (d, J =6 Hz, 1 H, 1α CH), 5.71 (dd, J=10.5 and 4 Hz, 1H, α CH of a leucine), 6.23 (s, 1H, 3a CH), 7.14 (d, J=8 Hz, 1H, CONH at 8), 7.53 (d, J=9 Hz, 1H, CONH at 5), 7.62 (mt, 1H, CONH at 7), 7.92 (d, J=10 Hz, 1H, CONH at 2).

Di[2-(1-piperidyl)ethyl] disulphide was prepared according to the following method:

127.7 cm$^3$ of triethylamine, followed by a solution of 57.78 g of iodine in 250 cm$^3$ of diethyl ether, were added dropwise over 10 minutes to a solution, cooled to 0° C., of 66 g of 2-(1-piperidyl)-ethanethiol in 850 cm$^3$ of dichloromethane. The mixture was stirred for 30 minutes at a temperature in the region of 20° C. and then taken up by 5 g of sodium sulphite in solution in 500 cm$^3$ of distilled water. The pH of the aqueous phase was adjusted to 9 by addition of a saturated aqueous potassium carbonate solution. The organic phase was separated by settling and the aqueous phase was extracted with a total of 600 cm$^3$ of dichloromethane. The combined organic phases were dried over magnesium sulphate and then concentrated under reduced pressure (2.7 kPa) at a temperature in the region of 40° C. to result in 56.5 g of di[2-(1-piperidyl)-ethyl] disulphide in the form of a brown oil used without additional purification.

2-(1-Piperidyl)ethanethiol was prepared according to the following method: a solution of 137 g of 2-(1-piperidyl) ethylisothiourea hydrochloride and of 84.3 g of sodium hydroxide in 1300 cm³ of distilled water was heated at reflux for 90 minutes. After having been brought back to a temperature in the region of 20° C., the mixture was neutralized (pH=7) by addition of concentrated hydrochloric acid. The mixture was extracted with a total of 450 cm³ of dichloromethane. The combined organic phases were washed with a total of 100 cm³ of distilled water, dried over magnesium sulphate and then concentrated under reduced pressure (2.7 kPa) at a temperature in the region of 40° C. to result in 66 g of 2-(1-piperidyl)ethanethiol in the form of an oil used without additional purification.

2-(1-Piperidyl)ethylisothiourea hydrochloride was prepared in the following way: A suspension of 100 g of N-(2-chloroethyl) piperidine hydrochloride and of 41.5 g of thiourea in 250 cm³ of dimethylformamide was heated at a temperature in the region of 110° C. for 2 hours. The mixture was cooled to a temperature in the region of 20° C. The white solid formed was subsequently filtered off, rinsed with a total of 100 cm³ of diethyl ether and dried under reduced pressure (10 kPa) at a temperature in the region of 40° C. to result in 134.1 g of 2-(1-piperidyl)-ethylisothiourea hydrochloride in the form of a white solid that melted at a temperature in the region of 240° C.

EXAMPLE 3

[(R)-2-(N-Methyl-N-t-butylamino)ethylthio-Sar]³-[4'-hydroxy-MeLeu]⁴-cyclosporin A was prepared according to the following method:

100 mg of sodium metal and then 100 mg of ferric nitrate were added to 720 cm³ of ammonia maintained at a temperature in the region of −33° C. As soon as the blue coloration of the mixture had disappeared, 6.50 g of sodium metal were added over 30 minutes. The mixture was stirred at −33° C. for 90 minutes, a solution of 24 g of [4'-hydroxy-MeLeu]⁴-cyclosporin A in 720 cm³ of t-butyl methyl ether was added dropwise over approximately 30 minutes and then a solution of 3.5 g of di[2-(N-methyl-N-t-butylamino) ethyl] disulphide in 120 cm³ of t-butyl methyl ether was added over 15 minutes. The reaction mixture was stirred at a temperature in the region of −33° C. for 30 minutes and then 24 g of solid ammonium chloride were added portionwise. The ammonia was allowed to evaporate with stirring, the temperature of the mixture changing from −33° C. to 25° C. over 12 hours. The reaction mixture was filtered. The solid was washed with a total of 1800 cm³ of diethyl ether. The combined organic phases were concentrated under reduced pressure (2.7 kPa) at a temperature in the region of 40° C. The residual oil (50.3 g) was triturated for 2 hours with 1200 cm³ of pentane. The solid obtained was filtered off and washed with 1800 cm³ of diethyl ether. The residual white solid (34.9 g) was purified by chromatography on a silica column (0.020–0.045 mm) (eluent: dichloromethane/ethanol 19/1 by volume). The fractions containing the expected product were concentrated under reduced pressure (2.7 kPa) at a temperature in the region of 40° C. and gave 8.9 g of a solid. This solid, triturated for 12 hours with pentane, gave, after filtration and drying at a temperature in the region of 40° C., 6.1 g of [(R)-2-(N-methyl-N-t-butylamino) ethylthio-Sar]³-[4'-hydroxy-MeLeu]⁴-cyclosporin A in the form of an off-white solid that melted at approximately 126–136° C.

¹H N.M.R. spectrum (400 MHz, CDCl₃, δ in ppm): 1.02 (s, the 9H corresponding to the C(CH₃)₃), 1.24 (mt, the 3H corresponding to the 8β CH₃), 1.33 (d, J=7.5 Hz, 3H, 7β CH₃), 1.61 (d, J=5 Hz, 3H, 1η CH₃), 1.69 and 2.36 (2dd, J=15 and 6.5 Hz, each 1H, 4β CH₂), 2.18 (broad s, 3H, NCH₃of the 2-(N-tert-butyl-N-methylamino)ethylthio at 3α), from 2.50 to 2.85 (mt, the 4H corresponding to the SCH₂CH₂N of the 2-(N-tert-butyl-N-methylamino)ethylthio at 3a), 2.70, 3.11, 3.14, 3.24, 3.43 and 3.48 (6 s, respectively 6H, 3H, 3H, 3H, 3H and 3H, the 7 NCH₃), 3.67 (mt, 1H, OH at 1β), 3.72 (mt, 1H, 1β CH), 4.52 (mt, 1H, 7α CH), 4.62 (broad t, J=9 Hz, 1H, 5α CH), 4.82 (mt, 1H, 8α CH), from 4.90 to 5.10 (mt, 3H, a CH of two 5 leucines and 2α CH), 5.11 (d, J=11 Hz, 1H, 11α CH), from 5.20 to 5.40 (mt, 2H, CH═CH), 5.41 (t, J=6.5 Hz, 1H, 4α CH), 5.48 (d, J=6 Hz, 1H, 1α CH), 5.68 (dd, J=10.5 and 4 Hz, 1H, α CH of a leucine), 5.87 (s, 1H, 3α CH), 7.14 (d, J=8Hz, 1H, CONH at 8), 7.48 (d, J=9 Hz, 1H, CONH at 5), 7.64 (d, J=8 Hz, 1H, CONH at 7), 7.94 (d, J=10Hz, 1H, CONH at 2).

Di[2-(N-methyl-N-t-butylamino)ethyl] disulphide was prepared in the following way:

0.1 cm³ of a 1N aqueous sodium hydroxide solution was added to a solution of 28.7 g of 2-(N-t-butyl-N-methylamino)ethanethiol in 190 cm³ of methanol and then a stream of air was passed through the mixture for 60 hours at a temperature in the region of 20° C. The methanol was removed under reduced pressure (2.7 kPa). The residual oil was dissolved in 400 cm³ of diethyl ether. The organic phase was dried over magnesium sulphate, filtered and then concentrated under reduced pressure (2.7 kPa) at a temperature in the region of 40° C. to result in 26.6 g of di[2-(N-methyl-N-t-butylamino)ethyl] disulphide in the form of a yellow oil.

2-(N-t-Butyl-N-methylamino)ethanethiol was prepared according to the following method:

A solution of 125 cm³ of N-t-butyl-N-methylamine and of 50 g of ethylene episulphide in 750 cm³ of t-butyl methyl ether was stirred for 48 hours at a temperature in the region of reflux. The mixture was concentrated under reduced pressure (10 kPa) at a temperature in the region of 35° C. Fractional distillation of the reaction mixture under reduced pressure (5.8 kPa) resulted in 28.7 g of 2-(N-t-butyl-N-methylamino)-ethanethiol in the form of a colourless oil that boiled between 84 and 86° C. at 5.8 kPa.

EXAMPLE 4

[(R)-2-(Hydroxy)ethylthio-Sar]³-[4'-hydroxy-MeLeu]⁴-cyclosporin A was prepared in the following way:

Hydroxylation with the *Sebekia benihana* strain was carried out as described hereinbelow: two 250 cm³ Erlenmeyer flasks, containing 50 cm³ of medium A (peptone: 10 g; yeast extract: 5 g; starch: 10 g; glucose: 5 g; agar: 11 g; water: q.s. for 1000 cm³; pH adjusted to 7.2; sterilization at 121° C. for 25 min.), were inoculated to the extent of 2% from two frozen liquid phials of the *Sebekia benihana* strain and were then incubated with shaking at 220 revolutions/min for 72 hours at a temperature in the region of 28° C. These two Erlenmeyer flasks constituted the inoculum Erlenmeyer flasks.

Sixteen 250 cm³ Erlenmeyer flasks containing 50 cm³ of medium B (glucose: 10 g; soluble starch: 10 g; yeast extract: 2.5 g; soybean flour: 12.5 g; dextrin: 10 g; potassium dihydrogenphosphate: 0.12 g; magnesium sulphate heptahydrate: 0.10 g; dipotassium hydrogen-phosphate: 0.25 g;

calcium chloride dihydrate: 0.05 g; [1 cm$^3$ of a solution containing: H$_3$BO$_3$: 0.1 g; FeSO$_4$.7H$_2$O: 5 g; KI: 0.05 g; CaCl$_2$.6H$_2$O: 2 g; CuSO.5H$_2$O: 0.2 g; MnCl$_2$.4H$_2$O: 2 g; ZnSO$_4$.7H$_2$O: 4 g; (NH$_4$)$_6$Mo$_7$O$_{24}$: 0.2 g; 97% H$_2$SO$_4$: 1 cm$^3$; water: q.s. for 1000 cm$^3$]; water: q.s. for 1000 cm$^3$; pH adjusted to 7.2–7.5; sterilization at 121° C. for 25 min), were inoculated to the extent of 4% from the inoculum Erlenmeyer flasks and were then incubated with shaking at 220 revolutions/min for 40 hours at a temperature in the region of 28° C. before addition of the product to be bioconverted. They constituted the production Erlenmeyer flasks.

A solution of 0.192 g of [(R)-2-(hydroxy)ethylthio-Sar]$^3$-cyclosporin A in 8 cm$^3$ of ethanol was prepared at the time of use and then filtered through a 0.2μ Millipore filter. 0.5 cm$^3$ of the mother solution of the [(R)-2-(hydroxy)ethylthio-Sar]$^3$cyclosporin A was added under sterile conditions to each of the production Erlenmeyer flasks. The Erlenmeyer flasks were incubated with shaking at 220 revolutions/min at a temperature in the region of 28° C. After 120 hours, each Erlenmeyer flask was extracted with 100 cm$^3$ of ethyl acetate. The 16 organic phases were combined, concentrated under reduced pressure (2.7 kPa) at a temperature in the region of 40° C. and then taken up in 20 cm$^3$ of methanol. 5 g of Sorbsil C60 (40–60 μm) silica (Prolabo) were added to the solution obtained and the entire contents were concentrated under reduced pressure (2.7 kPa) and then dried for 2 hours in an oven at a temperature in the region of 25° C. The residue was chromatographed on Sorbsil C60 (40–60 μm) silica (Prolabo) eluted with a 4/1 (by volume) mixture of ethyl acetate and of cyclohexane (throughput 20 cm$^3$/hour, 6-cm$^3$ fraction). Starting from fraction 6, elution was carried out with an ethyl acetate and methanol gradient. The expected product was eluted with 6% methanol. The fractions containing only the expected product were combined and evaporated under reduced pressure (2.7 kPa) at a temperature in the region of 40° C. The residue was taken up in 2 cm$^3$ of ethyl acetate and 10 cm$^3$ of cyclohexane and was then left for 2 hours at a temperature in the region of 4° C. The mixture was subsequently filtered, washed with heptane and concentrated to dryness (2.7 kPa) to give 10 mg of [(R)-2-(hydroxy)ethylthio-Sar]$^3$-[4'-hydroxy-MeLeu]$^4$-cyclosporin A in the form of a white powder.

$^1$H N.M.R. spectrum (400 MHz, CDCl$_3$, d in ppm): 1.26 (d, J=7.5 Hz, 3H, 8β CH$_3$), 1.37 (d, J=7.5 Hz, 3H, 7β CH$_3$), 1.64 (d, J=5 Hz, 3H, 1η CH$_3$), 2.68, 2.70, 3.13, 3.20, 3.25, 3.45 and 3.50 (7 s, each 3H, the 7 NCH$_3$), 2.83 (mt, 2H, SCH$_2$), 3.77 (mt, 1H, 1β CH), 3.82 (mt, 2H, CH$_2$O), 4.55 (mt, 1H, 7α CH), 4.67 (broad t, J=9 Hz, 1H, 5α CH), 4.85 (mt, 1H, 8α CH), 5.00 (dd, J=9 and 6 Hz, 1H, α CH of a leucine), from 5.00 to 5.10 (mt, 2H, α CH of a leucine and 2a CH), 5.13 (d, J=11 Hz, 1H, 11α CH), from 5.20 to 5.35 (mt, 2H, CH=CH), 5.40 (t, J=6.5 Hz, 1H, 4αCH), 5.49 (d, J=6 Hz, 1H, 1α CH), 5.71 (dd, J=10.5 and 4 Hz, 1H, α CH of a leucine), 5.92 (s, 1H, 3α CH), 7.17 (d, J=8 Hz, 1H, CONH at 8), 7.48 (d, J=9 Hz, 1H, CONH at 5), 7.64 (d, J=8Hz, 1H, CONH at 7), 7.95 (d, J=10Hz, 1H, CONH at 2).

[(R)-2-(hydroxy)ethylthio-Sar]$^3$-cyclosporin A was prepared according to the following method:

3.7 cm$^3$ of a 1M solution of tetrabutylammonium fluoride in tetrahydrofuran were added to a solution of 1.02 g of [(R)-2-(tert-butyldimethylsilyloxy)ethylthio-Sar]$^3$-cyclosporin A in 50 cm$^3$ of tetrahydrofuran. The mixture was stirred for 4 hours at a temperature in the region of 20° C. and then 50 cm$^3$ of distilled water were added to the mixture. The tetrahydrofuran was evaporated off under reduced pressure (2.7 kPa) at a temperature in the region of 40° C. The residue was treated with 50 cm$^3$ of ethyl acetate. The organic phase was separated by settling and the aqueous phase was extracted with a total of 100 cm$^3$ of ethyl acetate. The combined organic phases were washed with a total of 100 cm$^3$ of distilled water, dried over magnesium sulphate, filtered and then concentrated under reduced pressure (2.7 kPa) at a temperature in the region of 40° C. The residual solid (0.88 g) was purified by chromatography on a silica column (0.020–0.045 mm) (eluent: ethyl acetate), 15-cm$^3$ fractions were collected. The fractions containing the expected product (fractions 62 to 140) were combined and concentrated under reduced pressure (2.7 kPa) at a temperature in the region of 40° C. The residual solid (0.82 g) was purified by chromatography on a column of neutral alumina (eluent: ethyl acetate/cyclohexane 4/1 by volume), 5-cm$^3$ fractions were collected. The fractions containing the expected product (fractions 18 to 288) were combined and concentrated under reduced pressure (2.7 kPa) at a temperature in the region of 40° C. The residual solid (0.66 g) was treated with 50 cm$^3$ of ethyl acetate and the solution was filtered and then evaporated under reduced pressure (2.7 kPa) at a temperature in the region of 40° C. The residual solid was triturated with 50 cm$^3$ of diethyl ether and then filtered off and dried under reduced pressure (3 kPa) at a temperature in the region of 45° C. and gave 0.65 g of [(R)-2-(hydroxy)ethylthio-Sar]$^3$-cyclosporin A in the form of a white solid that melted at a temperature in the region of 139° C.

$^1$H N.M.R. spectrum (400 MHz, CDCl$_3$, δ in ppm): 1.26 (d, J=7.5 Hz, 3H, 8β CH$_3$), 1.36 (d, J=7.5 Hz, 3H, 7βCH$_3$), 1.64 (d, J=5 Hz, 3H, 1η CH$_3$), 2.70, 3.13, 3.14, 3.27, 3.47 and 3.51 (6 s, respectively 6H, 3H, 3H, 3H, 3H and 3H, the 7 NCH$_3$), 2.81 (t, J=6 Hz, 2H, SCH$_2$), 3.78 (mt, 1H, 1β CH), 3.86 (mt, 2H, CH$_2$O), 4.54 (mt, 1H, 7α CH), 4.66 (broad t, J=9 Hz, 1H, 5α CH), 4.84 (mt, 1H, 8α CH); 4.99 (dd, J=9 and 6 Hz, 1H, α CH of a leucine), from 5.00 to 5.10 (mt, 2H, a CH of a leucine and 2α CH), 5.13 (d, J=11 Hz, 1H, 11α CH), 5.24 (dd, J=11 and 4 Hz, 1H, α CH of a leucine), 5.33 (mt, 2H, CH=CH), 5.48 (d, J=6 Hz, 1H, 1α CH), 5.71 (dd, J=10.5 and 4 Hz, 1H, α CH of a leucine), 5.97 (s, 1H, 3α CH), 7.18 (d, J=8 Hz, 1H, CONH at 8), 7.30 (d, J=9 Hz, 1H, CONH at 5), 7.68 (d, J=8 Hz, 1H, CONH at 7), 7.98 (d, J=10 Hz, 1H, CONH at 2).

[(R)-2-(tert-butyidimethylsilyloxy)ethylthio-Sar]$^3$-cyclosporin A was prepared according to the following method:

100 mg of sodium metal and then 100 mg of ferric nitrate were added to 120 cm$^3$ of ammonia maintained at a temperature in the region of –33° C. As soon as the blue coloration of the mixture had disappeared, 1.3 g of sodium metal were added over 45 minutes. The mixture was stirred at –33° C. for 30 minutes and then a solution of 4.8 g of cyclosporin A in 120 cm$^3$ of tetrahydrofuran was added dropwise over approximately 30 minutes. The mixture was stirred for 30 minutes at a temperature in the region of –33° C. and then a solution of 30.56 g of di[2-(t-butyldimethylsilyloxy)ethyl] disulphide in 30 cm$^3$ of tetrahydrofuran was added over 20 minutes. The reaction mixture was stirred at a temperature in the region of –33° C. for 2 hours and then 4 g of solid ammonium chloride were added portionwise. The ammonia was allowed to evaporate with stirring, the temperature of the mixture changed from –33 to 250° C. over 19 hours. The mixture was diluted with 120 cm$^3$ of distilled water and then 120 cm$^3$ of diethyl ether. The organic phase was separated by settling and the aqueous phase was extracted with a total of 240 cm$^3$ of diethyl ether. The combined organic phases were washed with a total of 240 cm$^3$ of distilled water, dried over magnesium sulphate, filtered and then concentrated under reduced pressure (2.7 kPa) at a temperature in the region of 40° C. The residual solid (28.47 g) was purified by chromatography on a silica column (0.020–0.045 mm) (eluent: ethyl acetate/methanol 4/1 by volume), 100-cm³ fractions were collected. The fractions containing the expected product (fractions 58 to 95) were combined and concentrated under reduced pressure (2.7 kPa) at a temperature in the region of 40° C. to give 1.44 g of a foam. 0.2 g of this foam were treated with 2 cm³ of diethyl ether for 12 hours. After drying under reduced pressure (3 kPa) at a temperature in the region of 20° C., 0.13 g of [(R)-2- (tert-butyl-dimethylsilyloxy)ethylthio-Sar]³-cyclosporin A was obtained in the form of a beige solid melting at a temperature in the region of 125° C.

¹H N.M.R. spectrum (400 MHZ, CDCl₃, δ in ppm): 0.07 (s, 6H, Si(CH₃)₂), 1.26 (d, J=7.5Hz, 3H, 8βCH₃), 1.36 (d, J=7.5 Hz, 3H, 7β CH₃), 1.61 (d, J=5 Hz, 3H, 1η CH₃), 2.71, 3.10, 3.12, 3.27, 3.45 and 3.51 (6 s, respectively 6H, 3H, 3H, 3H, 3H and 3H, the 7 NCH₃), from 2.65 to 2.80 (mt, 2H, SCH₂), 3.63 (d, J=6 Hz, 1H, OH at 1β), 3.76 (mt, 1H, 1β CH), from 3.75 to 3.95 (mt, 2H, CH₂O), 4.53 (mt, 1H, 7α CH), 4.63 (broad t, J=9 Hz, 1H, 5α CH), 4.83 (mt, 1H, 8α CH), 4.96 (dd, J=9 and 6 Hz, 1H, α CH of a leucine), from 5.00 to 5.10 (mt, 2H, α CH of a leucine and 2α CH), 5.13 (d, J=11 Hz, 1H, 11α CH), 5.22 (dd, J=11.5 and 4 Hz, 1H, a CH of a leucine), 5.33 (mt, 2H, CH=CH), 5.48 (d, J=6 Hz, 1H, 1α CH), 5.70 (dd, J=10.5 and 4 Hz, 1H, α CH of a leucine), 6.00 (s, 1H, 3α CH), 7.16 (d, J=8 Hz, 1H, CONH at 8), 7.33 (d, J=9 Hz, 1H, CONH at 5), 7.66 (d, J=8 Hz, 1H, CONH at 7), 7.93 (d, J=10 Hz, 1H, CONH at 2).

Di[2-(t-butyidimethylsilyloxy)ethyl] disulphide was prepared according to the following method:

38.64 g of imidazole, in solution in 20 cm³ of dimethylformamide, were added dropwise to a solution, cooled to a temperature in the region of 0° C., of 15 cm³ of di[2-(hydroxy)ethyl] disulphide in 20 cm³ of dimethylformamide. The mixture was stirred for 30 minutes at 0° C. and then a suspension of 93 g of tert-butyidimethylchlorosilane in 200 cm³ of dimethylformamide was added while maintaining the temperature in the region of 0° C. The mixture was stirred for 30 minutes at a temperature in the region of 0°C. and then the mixture is reheated to a temperature in the region of 25° C. over 12 hours. The mixture was concentrated under reduced pressure (2.7 kPa) at a temperature in the region of 65° C. The residual oil was taken up in 100 cm³ of dichloromethane and 100 cm³ of distilled water. The organic phase was separated by settling and the aqueous phase was extracted with a total of 300 cm³ of dichloromethane. The organic phases were combined, dried over magnesium sulphate, filtered and then concentrated under reduced pressure (2.7 kPa) at a temperature in the region of 45° C. After removing the volatile compounds by distillation under reduced pressure (20 kPa) to a temperature in the region of 200° C., 41 g of di[2-(t-butyidimethylsilyloxy) ethyl] disulphide were obtained in the form of a yellow oil used in the preceding stage without additional purification.

EXAMPLE 5

[(R)-2-(N,N-diethylamino)ethylthio-Sar][4'-hydroxy-MeLeu]⁴-cyclosporin A was prepared according to the following method:

25 cm³ of ammonia were condensed in a reactor containing 0.89 g of sodamide and maintained at a temperature in the region of −33° C. and then a solution of 1.654 g of [4'-hydroxy-MeLeu]⁴-cyclosporin A in 20 cm³ of t-butyl methyl ether was added dropwise and with stirring over approximately 10 minutes. The mixture was stirred for 90 minutes at a temperature in the region of −33° C. and then 2.87 g of di[2-(N,N-diethylamino)ethyl] disulphide were added over approximately 5 minutes. The reaction mixture was stirred at a temperature in the region of −33° C. for 20 minutes and then 1.74 g of solid ammonium chloride were added in one portion. After stirring for 10 minutes, the ammonia was allowed to evaporate, the temperature of the mixture changed from −33 to 25° C. over 150 minutes. The reaction mixture was filtered. The solid was washed with a total of 8.8 cm³ of t-butyl methyl ether. The combined organic phases were concentrated to dryness under reduced pressure (2.7 kPa) at a temperature in the region of 40° C. The residual oil was stirred for 15 minutes with a mixture of 8 cm³ of n-hexane and 80 cm³ of heptane. The solid obtained was filtered and then rinsed with a total of 15 cm³ of n-heptane. The residual solid was dissolved in 25 cm³ of t-butyl methyl ether, 35 cm³ of distilled water were then added to the solution obtained and the pH of the aqueous phase was adjusted to 2 by addition of methanesulphonic acid. The organic phase was separated by settling and the aqueous phase was extracted with a total of 30 cm³ of t-butyl methyl ether. The combined aqueous phases were brought to pH=9 by addition of 20% aqueous ammonia. The aqueous phase was then extracted with a total of 25 cm³ of t-butyl methyl ether. The combined organic phases were dried over sodium sulphate, filtered and then concentrated under reduced pressure (2.7 kPa) at a temperature in the region of 40° C. The residual brown oil (1.5 g) was purified by chromatography on a column of neutral alumina eluted with a 9/1 (by volume) mixture of ethyl acetate and of ethanol. The fractions containing the expected product were concentrated under reduced pressure (2.7 kPa) at a temperature in the region of 40° C. to give 0.8 g of a solid. An aliquot of this solid (0.077 g) was purified by preparative silica thin layer chromatography (eluent: acetonitrile/methanol/28% ammonia, 260/40/3 (by volume)). The silica containing the expected product was removed and stirred with 5 cm³ of dichloromethane. After filtering and evaporating the organic phase under reduced pressure (2.7 kPa) at a temperature in the region of 40° C., 0.039 g of [(R)-2-(N,N-diethylamino) ethylthio-Sar]³-[4'-hydroxy-MeLeu]⁴-cyclosporin A was obtained in the form of an off-white amorphous solid that melted at approximately 140° C.

¹H N.M.R. spectrum (400 MHz, CDCl₃, δ in ppm): 1.34 (d, J=7.5 Hz, 3H, 7β CH₃), 1.60 (d, J=5 Hz, 3H, 1η CH₃), 1.68 and 2.36 (2 dd, J=15 and 6.5 Hz, each 1H, 4β CH₂), from 2.45 to 2.85 (mt, the 4H corresponding to the SCH₂CH₂N of the 2-diethylaminoethylthio at 3α), 2.51 (mt, the 4H corresponding to the 2 NCH₂ of the 2-diethylaminoethylthio at 3α), 2.70, 3.11, 3.18, 3.24, 3.44 and 3.49 (6 s, respectively 6H, 3H, 3H, 3H, 3H and 3H, 7 NCH₃), 3.63 (d, J=6 Hz, 1H, OH at 1), 3.74 (mt, 1H, 1β CH); 4.52 (mt, 1H, 7α CH), 4.61 (t, J=9 Hz, 1H, 5α CH), 4.81 (mt, 1H, 8α CH), 4.97 (dd, J=9 and 7 Hz, 1H, α CH of a leucine), from 5.00 to 5.10 (mt, 2H, 2α CH and α CH of a leucine), 5.12 (d, J=11 Hz, 1H, 11α CH), from 5.25 to 5.40 (mt, 2H, CH=CH), 5.40 (t, J=6.5 Hz, 1H, 4α CH), 5.47 (d, J=6 Hz, 1H, 1α CH), 5.68 (dd, J=10.5 and 4 Hz, 1H, α CH of a leucine), 5.96 (s, 1H, 3a CH), 7.13 (d, J=8 Hz, 1H, CONH at 8), 7.47 (d, J=9 Hz, 1H, CONH at 5), 7.61 (d, J=7.5 Hz, 1H, CONH at 7), 7.89 (d, J=9.5 Hz, 1H, CONH at 2).

Di(2-(N,N-diethylamino)ethyl) disulphide was prepared according to Bretschneider et al., Montatsh. Chem., 81, 385–396 (1950), the disclosure of which is incorporated herein by reference.

EXAMPLE 6

By carrying out the preparation in a way analogous to the method described in Example 1, the following compounds can be prepared:

[(R)-2-aminoethylthio-Sar]$^3$-[4'-hydroxy-MeLeu]$^4$-cyclosporin A;
[(R)-2-(N-methylamino)ethylthio-Sar]$^3$-[4'-hydroxy-MeLeu]$^4$-cyclosporin A;
[(R)-2-(N-ethylamino)ethylthio-Sar]$^3$-[4'-hydroxy-MeLeu]$^4$-cyclosporin A;
[(R)-2-(N-isopropylamino)ethylthio-Sar]$^3$-[4'-hydroxy-MeLeu]$^4$-cyclosporin A;
[(R)-2-(N-t-butylamino) ethylthio-Sar]$^3$-[4'-hydroxy-MeLeu]$^4$-cyclosporin A;
[(R)-2-(N-phenylamino) ethylthio-Sar]$^3$-[4'-hydroxy-MeLeu]$^4$-cyclosporin A;
[(R)-2-(N-benzylamino)ethylthio-Sar]$^3$-[4'-hydroxy-MeLeu]$^4$-cyclosporin A;
[(R)-2-(N-methyl-N-ethylamino)ethylthio-Sar]$^3$-[4'-hydroxy-MeLeu]$^4$-cyclosporin A;
[(R)-2-(N-methyl-N-isopropylamino)ethylthio-Sar]$^3$-[4'-hydroxy-MeLeu]$^4$-cyclosporin A;
[(R)-2-(N-methyl-N-tert-butylamino)ethylthio-Sar]$^3$-[4'-hydroxy-MeLeu]$^4$-cyclosporin A;
[(R)-2-(N-methyl-N-allylamino)ethylthio-Sar]$^3$-[4'-hydroxy-MeLeu]$^4$-cyclosporin A;
[(R)-2-(N-methyl-N-phenylamino)ethylthio-Sar]$^3$-[4'-hydroxy-MeLeu]$^4$-cyclosporin A;
[(R)-2-(N-methyl-N-benzylamino)ethylthio-Sar]$^3$-[4'-hydroxy-MeLeu]$^4$-cyclosporin A;
[(R)-2-(N,N-diethylamino)ethylthio-Sar]$^3$-[4'-hydroxy-MeLeu]$^4$-cyclosporin A;
[(R)-2-(N,N-diisopropylamino)ethylthio-Sar]$^3$-[4'-hydroxy-MeLeu]$^4$-cyclosporin A;
[(R)-2-(N, N-diallylamino)ethylthio-Sar]$^3$-[4'-hydroxy-MeLeu]$^4$-cyclosporin A;
[(R)-2-(I-piperidyl)ethylthio-Sar]$^3$-[4'-hydroxy-MeLeu]$^4$-cyclosporin A;
[(R)-3-aminopropylthio-Sar]$^3$-[4'-hydroxy-MeLeu]$^4$-cyclosporin A;
[(R)-3-(N-methylamino)propylthio-Sar]3-[4'-hydroxy-MeLeu]$^4$cyclosporin A;
[(R)-3-(N-ethylamino)propylthio-Sar]$^3$-[4'-hydroxy-MeLeu]$^4$-cyclosporin A;
[(R)-3-(N-isopropylamino)propylthio-Sar]3-[4'-hydroxy-MeLeu]$^4$-cyclosporin A;
[(R)-3-(N-tert-butylamino)propylthio-Sar]$^3$-[4'-hydroxy-MeLeu]$^4$-cyclosporin A;
[(R)-3-(N-phenylamino)propylthio-Sar]$^3$-[4'-hydroxy-MeLeu]$^4$-cyclosporin A;
[(R)-3-(N-benzylamino)propylthio-Sar]$^3$-[4'-hydroxy-MeLeu]$^4$-cyclosporin A;
[(R)-3-(N-methyl-N-ethylamino)propylthio-Sar]-[4'-hydroxy-MeLeu]$^4$-cyclosporin A;
[(R)-3-(N-methyl-N-isopropylamino)propylthio-Sar]$^3$-[4'-hydroxy-MeLeu]$^4$-cyclosporin A;
[(R)-3-(N-methyl-N-tert-butylamino)propylthio-Sar]$^3$-[4'-hydroxy-MeLeu]$^4$-cyclosporin A;
[(R)-3-(N-methyl-N-allylamino)propylthio-Sar]$^3$-[4'-hydroxy-MeLeu]$^4$-cyclosporin A;
[(R)-3-(N-methyl-N-phenylamino)propylthio-Sar]$^3$-[4'-hydroxy-MeLeu]$^4$-cyclosporin A;
[(R)-3-(N-methyl-N-benzylamino)propylthio-Sar]$^3$-[4'-hydroxy-MeLeu]$^4$-cyclosporin A;
[(R)-2-(N,N-dimethylamino)ethylthio-Sar]$^3$-[4'-hydroxy-MeLeu]$^4$-cyclosporin A;
[(R)-3-(N,N-diethylamino)propylthio-Sar]$^3$-[4'-hydroxy-MeLeu]$^4$-cyclosporin A;
[(R)-3-(N,N-diisopropylamino)propylthio-Sar]$^3$-[4'-hydroxy-MeLeu]$^4$-cyclosporin A;
[(R)-3-(N,N-diallylamino)propylthio-Sar]$^3$-[4'-hydroxy-MeLeu]$^4$-cyclosporin A;
[(R)-3-(1-piperidyl)propylthio-Sar]$^3$-[4'-hydroxy-MeLeu]$^4$-cyclosporin A;
[(R)-4-aminobutylthio-Sar]$^3$-[4'-hydroxy-MeLeu]$^4$-cyclosporin A;
[(R)-4-(N-methylamino)butylthio-Sar]$^3$-[4'-hydroxy-MeLeu]$^4$cyclosporin A;
[(R)-4-(N-ethylamino)butylthio-Sar]$^3$-[4'-hydroxy-MeLeu]$^4$-cyclosporin A;
[(R)-4-(N-isopropylamino)butylthio-Sar]$^3$-[4'-hydroxy-MeLeu]$^4$-cyclosporin A;
[(R)-4-(N-tert-butylamino)butylthio-Sar]$^3$-[4'-hydroxy-MeLeu]$^4$-cyclosporin A;
[(R)-4-(N-phenylamino)butylthio-Sar]$^3$-[4'-hydroxy-MeLeu]$^4$-cyclosporin A;
[(R)-4-(N-benzylamino)butylthio-Sar]$^3$-[4'-hydroxy-MeLeu]$^4$-cyclosporin A;
[(R)-4-(N-methyl-N-ethylamino)butylthio-Sar]$^3$-[4'-hydroxy-MeLeu]$^4$-cyclosporin A;
[(R)-4-(N-methyl-N-isopropylamino)butylthio-Sar]$^3$-[4'-hydroxy-MeLeu]$^4$-cyclosporin A;
[(R)-4-(N-methyl-N-tert-butylamino)butylthio-Sar]$^3$-[4'-hydroxy-MeLeu]$^4$-cyclosporin A;
[(R)-4-(N-methyl-N-allylamino)butylthio-Sar]$^3$-[4'-hydroxy-MeLeu]$^4$-cyclosporin A;
[(R)-4-(N-methyl-N-phenylamino)butylthio-Sar]$^3$-[4'-hydroxy-MeLeu]$^4$-cyclosporin A;
[(R)-4-(N-methyl-N-benzylamino)butylthio-Sar]$^3$-[4'-hydroxy-MeLeu]$^4$-cyclosporin A;
[(R)-4-(N,N-dimethylamino)butylthio-Sar]$^3$-[4'-hydroxy-MeLeu]$^4$-cyclosporin A;
[(R)-4-(N,N-diethylamino)butylthio-Sar]$^3$-[4'-hydroxy-MeLeu]$^4$-cyclosporin A;,
[(R)-4-(N,N-diisopropylamino)butylthio-Sar]$^3$- [4'-hydroxy-MeLeu]$^4$-cyclosporin A;
[(R)-4-(N,N-diallylamino)butylthio-Sar]$^3$-[4'-hydroxy-MeLeu]$^4$-cyclosporin A;
[(R)-4-(1-piperidyl)-butylthio-Sar]$^3$-[4'-hydroxy-MeLeu]$^4$-cyclosporin A;
[(R)-2-amino-2-methylpropylthio-Sar]$^3$-[4'-hydroxy-MeLeu]$^4$-cyclosporin A;
[(R)-2-(N,N-dimethylamino)-2-methylpropylthio-Sar]$^3$-[$^{4'}$-hydroxy-MeLeu]$^4$-cyclosporin A;
[(R)-2-(N,N-diethylamino)-2-methylpropylthio-Sar]$^3$-[4'-hydroxy-MeLeu]$^4$-cyclosporin A;
[(R)-2-(1-piperidyl)-2-methylpropylthio-Sar]$^3$-[4'-hydroxy-MeLeu]$^4$-cyclosporin A;
[(R)-3-amino-3-methylbutylthio-Sar]$^3$-[4'-hydroxy-MeLeu]$^4$-cyclosporin A;
[(R)-3-(N,N-dimethylamino)-3-methylbutylthio-Sar]$^3$-[4'-hydroxy-MeLeu]$^4$-cyclosporin A;
[(R)-3-(N, N-diethylamino)-3-methylbutylthio-Sar]$^3$-[4'-hydroxy-MeLeu]$^4$-cyclosporin A;
[(R)-3-(1-piperidyl)-3-methylbutylthio-Sar]$^3$-[4'-hydroxy-MeLeu]$^4$-cyclosporin A;
[(R)-2-(1-morpholino)ethylthio-Sar]$^3$-[4'-hydroxy-MeLeu]$^4$-cyclosporin A;
[(R)-2-(I-azetidino)ethylthio-Sar]$^3$-[4'-hydroxy-MeLeu]$^4$-cyclosporin A;
{(R)-2-[1-(methylpiperazino)-]ethylthio-Sar}$^3$-[4'-hydroxy-MeLeu]$^4$-cyclosporin A;
{(R)-2-[1-(4-phenylpiperazino)-]ethylthio-Sar}$^3$-[4'-hydroxy-MeLeu]$^4$-cyclosporin A;
{(R)-2-[1-(4-benzylpiperazino)-]ethylthio-Sar}$^3$-[4'-hydroxy-MeLeu]$^4$-cyclosporin A;
{(R)-2-[1-(4-methyl-1,2,3,6-tetrahydropyridyl)-]-ethylthio-Sar}$^3$-[4'-hydroxy-MeLeu]$^4$-cyclosporin A;
{(R)-2-[1-(4-phenyl-1,2,3,6-tetrahydropyridyl)-]-ethylthio-Sar}$^3$-[4'-hydroxy-MeLeu]$^4$-cyclosporin A;

[(R)-3-(1-morpholino)propylthio-Sar]³-[4'-hydroxy-MeLeu]⁴-cyclosporin A;
[(R)-3-(1-azetidino)propylthio-Sar]³-[4'-hydroxy-MeLeu]⁴-cyclosporin A;
{(R)-3-[1-(4-methylpiperazino)-]propylthio-Sar}³-[4'-hydroxy-MeLeu]⁴-cyclosporin A;
{(R)-3-[1-(4-phenylpiperazino)lpropylthio-Sar}³-[4'-hydroxy-MeLeu]⁴-cyclosporin A;
{(R)-3-[1-(4-benzylpiperazino)-]propylthio-Sar}³-[4'-hydroxy-MeLeu]⁴-cyclosporin A;
{(R)-3-[1-(4-methyl-1,2,3,6-tetrahydropyridyl)-]-propylthio-Sar}³-[4'-hydroxy-MeLeu]⁴-cyclosporin A; and
{(R)-3-[1-(4-methyl-1,2,3,6-tetrahydropyridyl)-]-propylthio-Sar}³-[4'-hydroxy-MeLeu]⁴-cyclosporin A.

The present invention also relates to pharmaceutical compositions containing at least one product of general formula (I), if appropriate in the salt form, either used alone or in the form of a combination with one or more compatible and pharmaceutically acceptable carriers, such as diluents or adjuvants, or with another anti-retrovirus agent, optionally intended for the treatment of AIDS, or an antiviral, immunomodulating or antimicrobial agent.

The composition according to the invention is capable of keeping alive cells infected with a retrovirus, such as, for example, the HIV, and thus of reducing progression towards AIDS or of decreasing its seriousness in subjects already infected by reducing the mortality of infected cells. The compositions can be used orally, parenterally, rectally or in aerosols.

The pharmaceutical compositions can be used curatively or preventively in subjects exhibiting immunodeficiency and/or infected by a retrovirus. Of course, the makeup of these compositions will be suited to the specific case of the digestive system of the immunodepressed subjects.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate.

These compositions can also contain adjuvants, in particular wetting, isotonizing, emulsifying, dispersing and stabilizing agents.

Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle with a particle size of 30 to 80 $\mu$m, for example dextran, mannitol or lactose.

In human therapeutics, the doctor will determine the posology which he considers most appropriate according to a preventive or curative treatment and according to the age, weight, stage of the infection and other factors specific to the subject to be treated. Generally, doses are between 5 and 30 mg/kg by the oral route for an adult.

In addition, it has been shown that cyclosporin compounds of formula (I) display a synergistic effect when they are combined with other antiviral agents that are active with respect to retroviruses. The present invention also relates to synergistic combinations which contain at least one cyclosporin compound of formula (I) and/or, if appropriate, their salts and an active principle known for its activity with respect to retroviruses.

The agents known for their activity with respect to retroviruses which can be combined are chosen from agents which are compatible and inert with respect to the cyclosporin compound of formula (I), both in the category of pharmacological treatments and in the category of alternative treatments, such as gene and cell or antisense therapy. Without implied limitation, these agents constituting the various therapeutic classes are chosen, for example, from nucleoside reverse transcriptase inhibitors (NRTI) and non-nucleoside reverse transcriptase inhibitors (NNRTI) [zidovudine (AZT), didanosine (DDI), dideoxycytidine (DDC), d4T, ribavirin, 3TC, nevirapin, and the like], from protease inhibitors [such as, for example, Saquinavir, Ritonavir, Indinavir and Nelfinavir], integrase inhibitors [such as AR177], from therapy gene inhibitors targeting the regulatory proteins of HIV replication, such as inhibitors of the rev protein [such as, for example, Rev M10], or nucleo-capsid inhibitors [such as, for example, DIBAs], from inhibitors targeting the specific messenger RNA transcripts of all the HIVs, such as, for example, the antisense ones [such as GEM92, GPI-2A and the like], from inhibitors of the family of modulators of cellular dNTP [such as hydroxyurea), from cytokine inhibitors [such as TNF], from inhibitors of entry of HIVs [such as T20, SPC-3, and the like], and from agents constituting therapeutic classes used in vaccinal approaches, both by biotechnology [such as HIVAC-1e, ALVAC, and the like] and by compounds acting with respect to the immune response [such as RG-8394].

The cyclosporin compound of Example 1 in particular displays a particularly advantageous synergistic effect when it is combined with AZT, ddl, Saquinavir, Nevirapin, Ritonavir and/or ribavirin and a likewise advantageous additive effect when combined with Indinavir.

The pharmaceutical compositions comprising such combinations, optionally in the presence of pharmaceutically acceptable excipients, are also within the scope of the present invention.

The following example illustrates a composition according to the invention.

FORMULATION EXAMPLE

A formulation was prepared which was administered by the oral route and which had the following composition:
[(R)-2-(N,N-Dimethylamino)ethylthio-Sar]³-[4'-hydroxy-MeLeu]4-cyclosporin A . . . 250 mg
Magnesium stearate . . . 3 mg Acdisol . . . 15 mg
Colloidal silica . . . 2 mg
Lactose . . . 130 mg

What is claimed is:

1. A cyclosporin compound of formula (I):

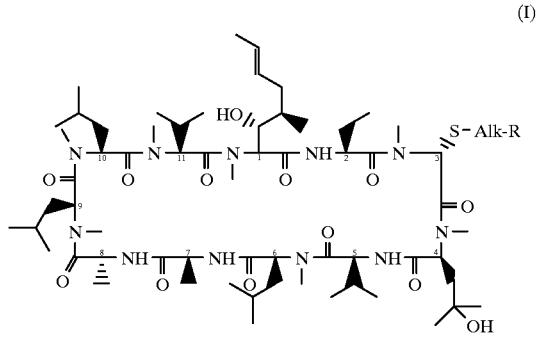

(I)

in which:

Alk represents a $C_{2-6}$ straight chain or branched alkylene radical or a $C_{3-6}$ cycloalkylene radical, and R represents
a hydroxyl radical,
a carboxyl radical,
an alkyloxycarbonyl radical,
an —$NR_1R_2$ radical in which $R_1$ and $R_2$, which are identical or different, represent a hydrogen atom or an alkyl, $C_{2-4}$ alkenyl, $C_{3-6}$ cycloalkyl or optionally substituted phenyl radical, wherein said phenyl radical may be substituted by a halogen atom, or an alkyloxy, alkyloxycarbonyl, amino, alkylamino or dialkylamino radical, or represent a benzyl or heterocyclyl radical, wherein said heterocyclyl radical may be saturated or unsaturated and contains 5 or 6 ring members and from 1 to 3 heteroatoms; or in which $R_1$ and $R_2$ form, together with the nitrogen atom to which they are attached, a saturated or unsaturated heterocycle containing 4 to 6 ring members, which heterocycle may optionally contain an additional heteroatom selected from nitrogen, oxygen and sulphur, and wherein said saturated or unsaturated heterocycle is optionally substituted by an alkyl, phenyl or benzyl radical, or
a radical of the formula (I'):

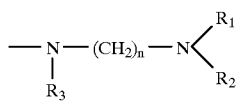

in which $R_1$ and $R_2$ are as defined above, $R_3$ represents a hydrogen atom or an alkyl radical, and n is an integer from 2 to 4;

wherein the alkyl portions or radicals defined above are straight chain or branched and contain from 1 to 4 carbon atoms;

or a pharmaceutically acceptable salt thereof.

2. A cyclosporin compound according to claim 1, in which:

Alk represents a $C_{2-6}$ straight chain or branched alkylene radical, and

R represents
a hydroxyl radical, or
an —$NR_1R_2$ radical in which $R_1$ and $R_2$, which are identical or different, represent a hydrogen atom or an alkyl, $C_{2-4}$ alkenyl or optionally substituted phenyl radical, wherein said phenyl radical may be substituted by a halogen atom or an alkyloxy, alkyloxycarbonyl, amino, alkylamino or dialkylamino radical, or represents a benzyl radical; or in which $R_1$ and $R_2$ form, together with the nitrogen atom to which they are attached, a saturated or unsaturated heterocycle containing 4 to 6 ring members, which heterocycle may optionally contain an additional heteroatom selected from nitrogen, oxygen and sulphur, and wherein said saturated or unsaturated heterocycle is optionally substituted by an alkyl radical;

or a pharmaceutically acceptable salt thereof.

3. A cyclosporin compound according to claim 1, wherein:

Alk represents a $C_{2-5}$ straight chain or branched alkylene radical, and

R represents
a hydroxyl radical, or
an —$NR_1R_2$ radical in which $R_1$ and $R_2$, which are identical or different, represent a hydrogen atom or an alkyl, allyl, phenyl or benzyl radical; or in which $R_1$ and $R_2$ form, together with the nitrogen atom to which they are attached, a heterocycle selected from azetidinyl, piperidyl, piperazinyl, N-methylpiperazinyl, N-phenylpiperazinyl, N-benzylpiperazinyl, morpholino, tetrahydropyridyl, methyltetrahydropyridyl and phenyltetrahydropyridyl;

or a pharmaceutically acceptable salt thereof.

4. A cyclosporin compound according to claim 1, which is [(R)-2-(N,N-dimethyl-amino)ethylthio-Sar]$^3$-[4'-hydroxy-MeLeu]$^4$-cyclosporin A, or a pharmaceutically acceptable salt thereof.

5. A cyclosporin compound according to claim 1, which is [(R)-2-(1-piperidyl)-ethylthio-Sar]$^3$-[4'-hydroxy-MeLeu]$^4$-cyclosporin A, or a pharmaceutically acceptable salt thereof.

6. A cyclosporin compound according to claim 1, which is [(R)-2-(N-methyl-N-t-butylamino)ethylthio-Sar]$^3$-[4'-hydroxy-MeLeu]$^4$-cyclosporin A, or a pharmaceutically acceptable salt thereof.

7. A cyclosporin compound according to claim 1, which is [(R)-2-(hydroxy)-ethylthio-Sar]$^3$-[4'-hydroxy-MeLeu]$^4$-cyclosporin A, or a pharmaceutically acceptable salt thereof.

8. A cyclosporin compound according to claim 1, which is [(R)-2-(N,N-diethyl-amino)ethylthio-Sar]$^3$-[4'-hydroxy-MeLeu]$^4$-cyclosporin A, or a pharmaceutically acceptable salt thereof.

9. A process for preparing a cyclosporin compound of formula (I) according to claim 1, said process comprising reacting a disulphide of the formula:

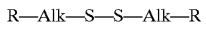

in which R and Alk are defined according to claim 1, in which any functional group in said cyclosporin compound of formula (II) below capable of interfering with said reaction has been protected with a protecting radical, with an activated form of a [4,-hydroxy-MeLeu]$^4$-cyclosporin derivative of the formula (II):

(II)

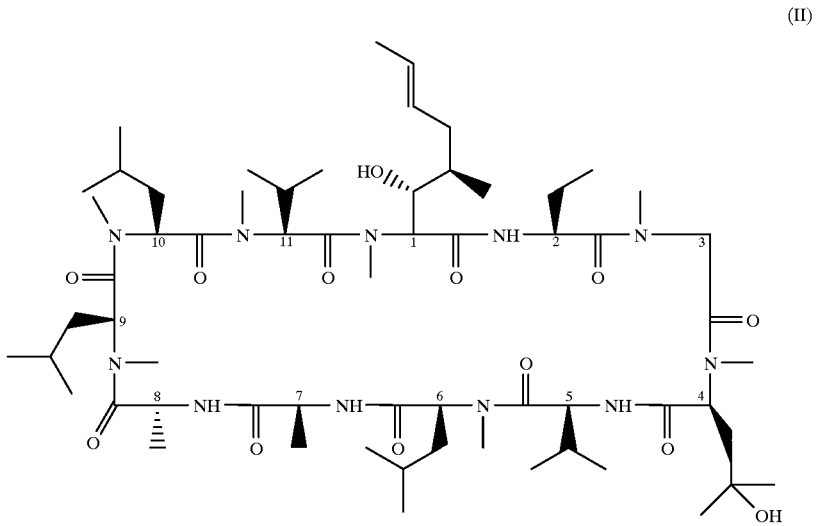

removing, if appropriate, said protective radical(s), and optionally converting the product of said reaction into a salt.

10. A pharmaceutical composition, said composition comprising at least one cyclosporin compound of formula (I) according claim 1, said cyclosporin compound being present alone or in combination with a compatible and pharmaceutically acceptable carrier.

11. A pharmaceutical composition according to claim 10, wherein said composition further comprises at least one antiviral, immunomodulating or antimicrobial active principle.

12. A combination comprising at least one cyclosporin compound of formula (I) according to claim 1 and further comprising at least one anti-retroviral agent.

13. A combination according to claim 12, wherein said at least one anti-retroviral agent is AZT, ddl, Saquinavir, Nevirapin, Ritonavir or ribavirin.

14. A combination comprising [(R)-2-(N,N-dimethylamino)ethylthio-Sar]$^3$-[4'-hydroxy-MeLeu]$^4$-cyclosporin A or a pharmaceutically acceptable salt thereof and further comprising at least one additional anti-retroviral agent.

15. A combination according to claim 14, wherein said at least one anti-retroviral agent is AZT, ddl, Saquinavir, Nevirapin, Ritonavir or ribavirin.

16. A synergistic combination comprising at least one cyclosporin derivative of formula (I) according to claim 1 and further comprising at least one anti-retroviral agent.

17. A combination according to claim 16, wherein said at least one anti-retroviral agent is Indinavir.

18. A method for treating a retrovirus, said method comprising administering to a host for the purpose of said prevention or treatment an effective amount of a cyclosporin compound of formula (I) or a salt thereof according to claim 1.

19. A method according to claim 18, wherein said retrovirus is AIDS or an AIDS associated syndrome.

20. A method according to claim 18, wherein said effective amount of said cyclosporin compound of formula (I) or salt thereof is a concentration of 10 to 350 nM.

21. A compound selected from:

[(R)-2-aminoethylthio-Sar]$^3$-[4'-hydroxy-MeLeu]$^4$-cyclosporin A;

[(R)-2-(N-methylamino)ethylthio-Sar]$^3$-[$^{4'}$-hydroxy-MeLeu]$^4$-cyclosporin A;

[(R)-2-(N-ethylamino)ethylthio-Sar]$^3$-[4'-hydroxy-MeLeu]$^4$-cyclosporin A;

[(R)-2-(N-isopropylamino)ethylthio-Sar]$^3$-[4'-hydroxy-MeLeu]$^4$-cyclosporin A;

[(R)-2-(N-t-butylamino)ethylthio-Sar]$^3$-[4'-hydroxy-MeLeu]$^4$-cyclosporin A;

[(R)-2-(N-phenylamino)ethylthio-Sar]$^3$-[4'-hydroxy-MeLeu]$^4$-cyclosporin A;

[(R)-2-(N-benzylamino)ethylthio-Sar]$^3$-[4'-hydroxy-MeLeu]$^4$-cyclosporin A;

[(R)-2-(N-methyl-N-ethylamino)ethylthio-Sar]$^3$-[4'-hydroxy-MeLeu]$^4$-cyclosporin A;

[(R)-2-(N-methyl-N-isopropylamino)ethylthio-Sar]$^3$-[4'-hydroxy-MeLeu]$^4$-cyclosporin A;

[(R)-2-(N-methyl-N-tert-butylamino)ethylthio-Sar]$^3$-[4'-hydroxy-MeLeu]$^4$-cyclosporin A;

[(R)-2-(N-methyl-N-allylamino)ethylthio-Sar]$^3$-[4'-hydroxy-MeLeu]$^4$-cyclosporin A;

[(R)-2-(N-methyl-N-phenylamino)ethylthio-Sar]$^3$-[4'-hydroxy-MeLeu]$^4$-cyclosporin A;

[(R)-2-(N-methyl-N-benzylamino)ethylthio-Sar]$^3$-[4'-hydroxy-MeLeu]$^4$-cyclosporin A;

[(R)-2-(N,N-diethylamino)ethylthio-Sar]$^3$-[4'-hydroxy-MeLeu]$^4$-cyclosporin A;

[(R)-2-(N,N-diisopropylamino)ethylthio-Sar]$^3$-[4'-hydroxy-MeLeu]$^4$-cyclosporin A;

[(R)-2-(N, N-diallylamino)ethylthio-Sar]$^3$-[4'-hydroxy-MeLeu]$^4$-cyclosporin A;

[(R)-2-(I-piperidyl)ethylthio-Sar]$^3$-[4'-hydroxy-MeLeu]$^4$-cyclosporin A;

[(R)-3-aminopropylthio-Sar]$^3$-[4'-hydroxy-MeLeu]$^4$-cyclosporin A;

[(R)-3-(N-methylamino)propylthio-Sar]$^3$-[4'-hydroxy-MeLeu]$^4$-cyclosporin A;

[(R)-3-(N-ethylamino)propylthio-Sar]$^3$-[4'-hydroxy-MeLeu]$^4$-cyclosporin A;

[(R)-3-(N-isopropylamino)propylthio-Sar]$^3$-[4'-hydroxy-MeLeu]$^4$-cyclosporin A;

[(R)-3-(N-tert-butylamino)propylthio-Sar]$^3$-[4'-hydroxy-MeLeu]$^4$-cyclosporin A;

[(R)-3-(N-phenylamino)propylthio-Sar]$^3$-[4'-hydroxy-MeLeu]$^4$-cyclosporin A;

[(R)-3-(N-benzylamino)propylthio-Sar]³-[4'-hydroxy-MeLeu]⁴-cyclosporin A;
[(R)-3-(N-methyl-N-ethylamino)propylthio-Sar]³-[4'-hydroxy-MeLeu]⁴-cyclosporin A;
[(R)-3-(N-methyl-N-isopropylamino)propylthio-Sar]³-[4'-hydroxy-MeLeu]⁴-cyclosporin A;
[(R)-3-(N-methyl-N-tert-butylamino)propylthio-Sar]³-[4'-hydroxy-MeLeu]⁴-cyclosporin A;
[(R)-3-(N-methyl-N-allylamino)propylthio-Sar]³-[4'-hydroxy-MeLeu]⁴-cyclosporin A;
[(R)-3-(N-methyl-N-phenylamino)propylthio-Sar]³-[4'-hydroxy-MeLeu]⁴-cyclosporin A;
[(R)-3-(N-methyl-N-benzylamino )propylthio-Sar]³-[4'-hydroxy -MeLeu]⁴-cyclosporin A;
[(R)-2-(N,N-dimethylamino)ethylthio-Sar]³-[4'-hydroxy-MeLeu]⁴-cyclosporin A;
[(R)-3-(N,N-diethylamino)propylthio-Sar]³-[4'-hydroxy-MeLeu]⁴-cyclosporin A;
[(R)-3-(N,N-diisopropylamino)propylthio-Sar]³-[4'-hydroxy-MeLeu]⁴-cyclosporin A;
[(R)-3-(N,N-diallylamino)propylthio-Sar]³-[4'-hydroxy-MeLeu]⁴-cyclosporin A;
[(R)-3-(1-piperidyl)propylthio-Sar]³-[4'-hydroxy-MeLeu]⁴-cyclosporin A;
[(R)-4-aminobutylthio-Sar]³-]4'-hydroxy-MeLeu]⁴-cyclosporin A;
[(R)-4-(N-methylamino)butylthio-Sar]³-[4'-hydroxy-MeLeu]⁴-cyclosporin A;
[(R)-4-(N-ethylamino)butylthio-Sar]³-[4'-hydroxy-MeLeu]⁴-cyclosporin A;
[(R)-4-(N-isopropylamino)butylthio-Sar]³ [4'-hydroxy-MeLeu]⁴-cyclosporin A;
[(R)-4-(N-tert-butylamino)butylthio-Sar]³-[4'-hydroxy-MeLeu]⁴-cyclosporin A;
[(R)-4-(N-phenylamino)butylthio-Sar]³-[4'-hydroxy-MeLeu]⁴-cyclosporin A;
[(R)-4-(N-benzylamino)butylthio-Sar]³-[4'-hydroxy-MeLeu]⁴-cyclosporin A;
[(R)-4-(N-methyl-N-ethylamino)butylthio-Sar]³-[4'-hydroxy-MeLeu]⁴-cyclosporin A;
[(R)-4-(N-methyl-N-isopropylamino)butylthio-Sar]³-[4'-hydroxy-MeLeu]⁴-cyclosporin A;
[(R)-4-(N-methyl-N-tert-butylamino)butylthio-Sar]³-[4'-hydroxy-MeLeu]⁴-cyclosporin A;
[(R)-⁴-(N-methyl-N-allylamino)butylthio-Sar]³-[4'-hydroxy-MeLeu]⁴-cyclosporin A;
[(R)-⁴-(N-methyl-N-phenylamino)butylthio-Sar]³-[4'-hydroxy-MeLeu]⁴-cyclosporin A;
[(R)-⁴-(N-methyl-N-benzylamino)butylthio-Sar]³-[4'-hydroxy-MeLeu]⁴-cyclosporin A;
[(R)-⁴-(N,N-dimethylamino)butylthio-Sar]³-[4'-hydroxy-MeLeu]⁴-cyclosporin A;
[(R)-⁴-(N,N-diethylamino)butylthio-Sar]³-[4'-hydroxy-MeLeu]⁴-cyclosporin A;
[(R)-⁴-(N,N-diisopropylamino)butylthio-Sar]³-[4'-hydroxy-MeLeu]⁴-cyclosporin A;
[(R)-⁴-(N,N-diallylamino)butylthio-Sar]³-[4'-hydroxy-MeLeu]⁴-cyclosporin A;
[(R)-⁴-(1-piperidyl)-butylthio-Sar]³-[4'-hydroxy-MeLeu]⁴-cyclosporin A;
[(R)-2-amino-2-methylpropylthio-Sar]³-[4'-hydroxy-MeLeu]⁴-cyclosporin A;
[(R)-2-(N,N-dimethylamino)-2-methylpropylthio-Sar]³-[4'-hydroxy-MeLeu]⁴-cyclosporin A;

[(R)-2-(N,N-diethylamino)-2-methylpropylthio-Sar]³-[4'-hydroxy-MeLeu]⁴-cyclosporin A;
[(R)-2-(1-piperidyl)-2-methylpropylthio-Sar]³-[4'-hydroxy-MeLeu]⁴-cyclosporin A;
[(R)-3-amino-3-methylbutylthio-Sar]³-[4'-hydroxy-MeLeu]⁴-cyclosporin A;
[(R)-3-(N,N-dimethylamino)-3-methylbutylthio-Sar]³-[4'-hydroxy-MeLeu]⁴-cyclosporin A;
[(R)-3-(N,N-diethylamino)-3-methylbutylthio-Sar]³-[4'-hydroxy-MeLeu]⁴-cyclosporin A;
[(R)-3-(1-piperidyl)-3-methylbutylthio-Sar]³-[4'-hydroxy-MeLeu]⁴-cyclosporin A;
[(R)-2-(1-morpholino)ethylthio-Sar]³-[4'-hydroxy-MeLeu]⁴-cyclosporin A;
[(R)-2-(I-azetidino)ethylthio-Sar]³-[4'-hydroxy-MeLeu]⁴-cyclosporin A;
{(R)-2-[1-(methylpiperazino)-]ethylthio-Sar}³-[4'-hydroxy-MeLeu]⁴-cyclosporin A;
{(R)-2-[1-(4-phenylpiperazino)-]ethylthio-Sar}³-[4'-hydroxy-MeLeu]⁴-cyclosporin A;
{(R)-2-[1-(4-benzylpiperazino)-]ethylthio-Sar}³-[4'-hydroxy-MeLeu]⁴-cyclosporin A;
{(R)-2-[1-(4-methyl-1,2,3,6-tetrahydropyridyl)-]ethylthio-Sar}³-[4'-hydroxy-MeLeu]⁴-cyclosporin A;
{(R)-2-[1-(4-phenyl-1,2,3,6-tetrahydropyridyl)-]ethylthio-Sar}³-[4'-hydroxy-MeLeu]⁴-cyclosporin A;
[(R)-3-(1-morpholino)propylthio-Sar]³-[4'-hydroxy-MeLeu]⁴-cyclosporin A;
[(R)-3-(1-azetidino)propylthio-Sar]³-[4'-hydroxy-MeLeu]⁴-cyclosporin A;
{(R)-3-[1-(4-methylpiperazino)-]propylthio-Sar}³-[4'-hydroxy-MeLeu]⁴-cyclosporin A;
{(R)-3-[1-(4-phenylpiperazino)-]propylthio-Sar}³-[4'-hydroxy-MeLeu]⁴-cyclosporin A;
{(R)-3-[1-(4-benzylpiperazino)-]propylthio-Sar}³-[4'-hydroxy-MeLeu]⁴-cyclosporin A;
{(R)-3-[1-(4-methyl-1,2,3,6-tetrahydropyridyl)-]propylthio-Sar}³-[⁴'-hydroxy-MeLeu]⁴-cyclosporin A; and
{(R)-3-[1-(4-methyl-1,2,3,6-tetrahydropyridyl)-]propylthio-Sar}³-[⁴'-hydroxy-MeLeu]⁴-cyclosporin A,
or their pharmaceutically acceptable salts.

22. A cyclosporin compound of formula (I):

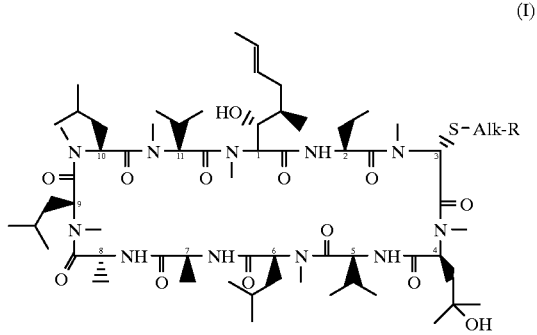

(I)

in which
Alk represents a $C_{2-6}$ straight chain or branched alkylene radical or a $C_{3-6}$ cycloalkylene radical, and
R represents
a hydroxyl radical,
a carboxyl radical,
an alkyloxycarbonyl radical, an —NR$_1$R$_2$ radical in which R$_1$ and R$_2$, which are identical or different, represent a hydrogen atom or an alkyl, C$_{3-6}$ cycloalkyl or optionally substituted phenyl radical, wherein said phenyl radical may be substituted by a halogen atom, or an alkyloxy, alkyloxycarbonyl, amino, alkylamino or dialkylamino radical, or represent a benzyl or heterocyclyl radical, wherein said heterocyclyl radical may be saturated or unsaturated and contains 5 or 6 ring members and from 1 to 3 heteroatoms; or in which R$_1$ and R$_2$ form, together with the nitrogen atom to which they are attached, a saturated or unsaturated heterocycle containing 5 to 6 ring members, which heterocycle may optionally contain an additional heteroatom selected from nitrogen, oxygen and sulphur, and wherein said saturated or unsaturated heterocycle is optionally substituted by an alkyl radical, or a radical of the formula (I'):

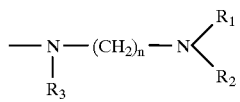

in which R$_1$ and R$_2$ are as defined above, R$_3$ represents a hydrogen atom or an alkyl radical, and n is an integer from 2 to 4;

wherein the alkyl portions or radicals defined above are straight chain or branched and contain from 1 to 4 carbon atoms;

or a pharmaceutically acceptable salt thereof.

* * * * *

UNITED STATES PATENT AND TRADEMARK OFFICE
CERTIFICATE OF CORRECTION

PATENT NO. : 5,994,299
DATED : November 30, 1999
INVENTOR(S) : Jean-Claude Barriere, Georges Bashiardes, Jean-Christophe Carry, Bruno Filoche and Serge Mignani  Michel Evers, It is certified that error appears in the above-identified patent and that said Letters Patent is hereby corrected as shown below:

Claim 21, column 21, line 66, "[$4"$-hydroxy-" should read -- [4'-hydroxy- --;

column 23, lines 47, 49, 51, 53, 55, 57, 59 and 61, "[(R)-$^4$-" should read -- [(R) -4- --; and column 24, lines 39 and 43, "[$4"$-hydroxy-MeLeu]$^{4"}$" should read -- [4'-hydroxy-MeLeu]$^4$ --.

Signed and Sealed this

Twelfth Day of September, 2000

Attest:

Q. TODD DICKINSON

*Attesting Officer*  *Director of Patents and Trademarks*